United States Patent [19]

DeArdo

[11] 4,004,066
[45] Jan. 18, 1977

[54] METHOD OF PROTECTING CONCRETE

[75] Inventor: Anthony J. DeArdo, New Kensington, Pa.

[73] Assignee: Aluminum Company of America, Pittsburgh, Pa.

[22] Filed: Aug. 6, 1975

[21] Appl. No.: 602,266

[52] U.S. Cl. .............................. 428/538; 106/90; 252/142; 134/3; 428/304; 428/543
[51] Int. Cl.² ...................................... B32B 9/04
[58] Field of Search ................. 428/538, 543, 304; 252/388, 142; 52/723; 264/333; 260/535 P, 535 R; 106/14, 102, 90; 134/3; 427/136

[56] References Cited

FOREIGN PATENTS OR APPLICATIONS 17,426 2/1975 Japan
98,832 9/1974 Japan

Primary Examiner—George F. Lesmes
Assistant Examiner—P. J. Thibodeau
Attorney, Agent, or Firm—John P. Taylor

[57] ABSTRACT

Concrete is protected from attack by organic lubricants by treating it with an aqueous solution of citric acid.

4 Claims, 2 Drawing Figures

METHOD OF PROTECTING CONCRETE

BACKGROUND OF THE INVENTION

This invention relates to the protection of concrete from attack by organic lubricating materials.

Industrial plants processing metals such as metal rolling mills use lubricants such as fatty acids and esters which create a major problem with respect to concrete foundation materials including plant floors, mill foundations, pits, motor and pump pedestals, and the like. To overcome this problem of concrete attack by such acids and esters, coal tar epoxy coatings, epoxy cements, and steel plates covering the concrete surfaces have been used with some degree of success. However, each of these solutions has had its limitations. Coal tar epoxy coatings tend to crack easily when subject to vibrations permitting the lubricant to undermine the coating. Epoxy cements are relatively expensive. Steel plate covering the concrete has been the best solution. However, all concrete surfaces cannot be covered and there is an occasional broken weld which allows the aggressive rolling lubricants to attack the concrete behind or beneath the steel.

Quite surprisingly, it has now been discovered that concrete deterioration from attack by such fatty acids and esters can be inhibited by a preliminary treatment of the concrete.

SUMMARY OF THE INVENTION

In accordance with the invention, concrete is treated to inhibit attack by organic lubricating materials by treating the concrete for at least about 1 hour with an aqueous solution of citric acid. Preferably, the concrete is treated after about 28 days of curing.

DESCRIPTION OF THE INVENTION

Figure 1:
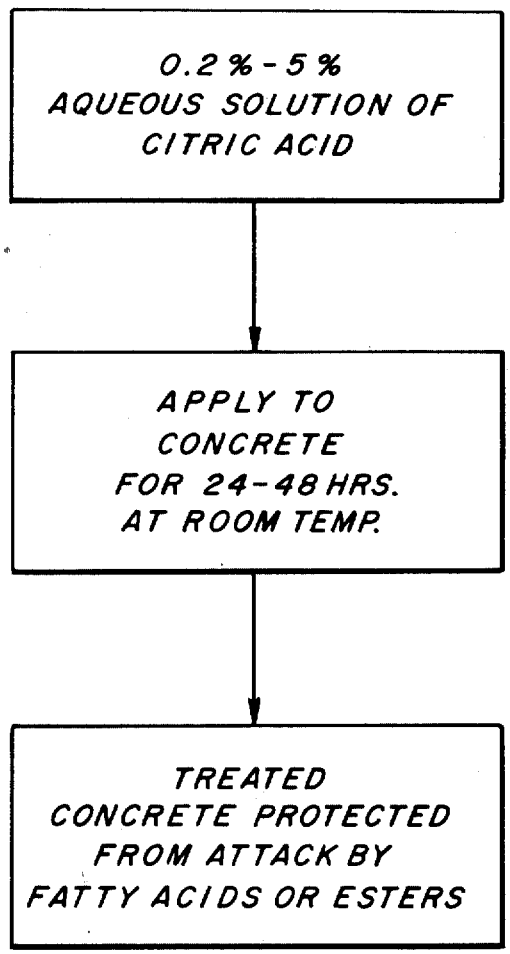
FIG. 1 is a flowsheet of the invention.

In accordance with the invention, concrete is protected from the deleterious effects of fatty acids and esters such as butyl stearate and the like by treating the concrete with a solution of citric acid.

Conveniently, the citric acid can be applied as an aqueous solution by dissolving the normally solid citric acid in water to the desired concentration. While as little as 0.1% by weight citric acid can be used, preferably the amount used is at least about 0.2% and most preferably at least about 0.5% by weight. While the maximum amount used will vary only with economics, conveniently not more than about 5% by weight need be used. The reaction time period has been found to be dependent upon the concentration of the citric acid. For example, when a 5% solution is used, 1 hour of reaction time is sufficient, while less concentrated amounts require more time, e.g. 0.2% may require as much as 48 hours. For smaller parts the concrete may be immersed in a citric acid bath. Alternatively, the concrete area to be treated may be flooded with an aqueous citric acid solution. The solution can be applied to the concrete at ambient temperature, although the use of higher temperatures has not been found to be deleterious.

While there is no intention to be bound by any particular theory as to the mechanism, it is believed that the citric acid inhibits concrete deterioration by fatty acids and esters such as butyl stearate or the like in that it reacts with the free calcium in the cement to form calcium citrate, an inhibiting whitish deposit, on the concrete surface. When the organic lubricating material comes in contact with this treated surface, it would appear that deterioration may be inhibited by the absence of free calcium to react with the organic lubricating material.

While the citric acid may be applied to the concrete at any stage of the life of the concrete, it has been found to be most effective if applied on new concrete after it has been allowed to set for about 28 days. Citric acid has also been incorporated into the slurry concrete mix prior to curing and has been incorporated into the lubricant itself. Neither has been found as effective as the aqueous treatment of the cured concrete in accordance with the invention.

The following examples will serve to further illustrate the invention:

EXAMPLE I

A series of test concrete coupons were made by mixing together 1 part by weight of Type I portland cement with 2 parts by weight sand and 3 parts by weight shot gravel having a particle size range of about ½ inch to No. 8 (as specified in ASTM C33-74 specification). This dry mixture is then blended with about 0.6 parts by weight water. The mix is poured into 8-ounce cup molds and cured at 100% humidity for 28 days. The samples were then treated in citric acid at a concentration of from 0.25% to 5% by weight for varying time periods at room temperature except for one treatment which was made at 120° F. Two samples were not treated in citric acid and were used as controls. Each of the samples were then immersed in butyl stearate for varying times and at varying temperatures. As noted in the table below, two different butyl stearates were used; one obtained from Commercial Solvents Corporation as a clear water white material and the other from the Harshaw Chemical Company as a brown material. In one instance, one of the controls was immersed in a mill solution containing fatty acids and ester as well as .02% citric acid to illustrate whether or not the use of citric acid in situ with the organic lubricant provided any effect. (This amount, while lower than the amount used in the pre-treatment, was the highest amount which could be used in the lubricating system without affecting the overall quality of the lubricant.) Results are contained in Table I below:

TABLE I

| Citric Acid Treatment | | | Static Beaker Test | | | |
|---|---|---|---|---|---|---|
| Citric Acid Conc. in DI Water | Temp. | Time | Solution | Temp. | Time (days) | Remarks |
| 1. None | | | Rolling mill solution containing fatty acids, esters, and 0.02% citric acid | 120° F | 60 | Light concrete attack |

TABLE I-continued

| | Citric Acid Treatment | | | Static Beaker Test | | | |
|---|---|---|---|---|---|---|---|
| | Citric Acid Conc. in DI Water | Temp. | Time | Solution | Temp. | Time (days) | Remarks |
| 2. | 5% | 120° F | 30 days | Butyl Stearate (CC) | ambient | 33 | No deterioration |
| 3. | 5% | R.T. | 1 hr. | Butyl Stearate (CC) | 120° F | 30 | No deterioration |
| 4. | 5% | R.T. | 2 hrs. | Butyl Stearate (CC) | 120° F | 30 | No deterioration |
| 5. | 5% | R.T. | 1 hr. | Butyl Stearate (H) | ambient | 30 | No deterioration |
| 6. | 5% | R.T. | 2 hrs. | Butyl Stearate (H) | ambient | 30 | No deterioration |
| 7. | 2.5% | R.T. | 24 hrs. | Butyl Stearate (H) | ambient | 30 | No deterioration |
| 8. | 5% | R.T. | 2 hrs. | Butyl Stearate (CC) | ambient | 24 | No deterioration |
| 9. | 0.25% | R.T. | 7 days | Butyl Stearate (CC) | ambient | 35 | No attack |
| 10. | 0.5% | R.T. | 7 days | Butyl Stearate (CC) | ambient | 35 | No attack |
| 11. | 0.5% | R.T. | 7 days | Butyl Stearate (CC) | ambient | 30 | No attack |
| 12. | None | — | — | Butyl Stearate (CC) | ambient | 21 | Severe attack |

CC - Commercial Solvents Corporation
H - Harshaw Chemical Company

Figure 2:
FIG. 2 is a photolithographic reproduction of samples respectively treated with varying amounts of citric acid as well as one sample having no citric acid treatment.

The results clearly show that the citric acid treated samples resisted attack by butyl stearate while the sample having no citric acid pre-treatment was severely attacked. It is also noted that there was some attack on the sample in which the citric acid was incorporated into the lubricant rather than applied in a pre-treatment. FIG. 2 depicts the results obtained with Samples 5, 9, 11, and 12.

EXAMPLE II

To protect the concrete in a large oil pit or cellar in accordance with the invention, a pit or cellar having dimensions of 40 feet by 20 feet is filled to a height of 2 feet with an 0.5% solution of citric acid and water by first filling the cellar with water to a height of about 12 inches using about 6,000 gallons of water. The citric acid is then added to the water by emptying a 100-pound bag of citric acid into a 55-gallon drum and filling the drum with water to provide agitation to stir the citric into solution. Five such drums, i.e. 500 pounds of citric acid, are used. This concentrated citric acid is poured into the cellar at various locations to obtain better distribution. Another 6,000 gallons of water is then added to bring the level up to 2 feet. The addition of the second 6,000 gallons is also used to provide additional agitation to thoroughly mix the concentrated citric acid into the water. The citric acid solution is then allowed to react with the concrete for about 48 hours. If the walls of the cellar are higher than 2 feet, they may be wet down with the citric acid using a suction hose and a pump to wet down the walls. After the 48-hour pre-treatment, the citric acid solution is drained from the cellar. The concrete is then ready for use in an environment to which it will be exposed to fatty acids and esters without experiencing the concrete deterioration of unprotected concrete.

Having thus described the invention, what is claimed is:

1. A method of protecting cured concrete from attack by organic lubricants which comprises treating the cured concrete for at least 1 hour with an aqueous solution of citric acid having a concentration of from 0.1% to 5% by weight.

2. The method of claim 1 wherein said concrete has been allowed to cure for at least 28 days prior to treatment.

3. The method of claim 1 wherein said treatment is carried out under ambient conditions.

4. The method of claim 1 wherein the concentration of said citric acid is at least 0.2% by weight.

* * * * *